United States Patent
Yamamoto

(10) Patent No.: US 8,685,197 B2
(45) Date of Patent: Apr. 1, 2014

(54) METHOD OF MANUFACTURING ABSORBENT ARTICLE

(75) Inventor: Hiroki Yamamoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 254 days.

(21) Appl. No.: 12/715,813

(22) Filed: Mar. 2, 2010

(65) Prior Publication Data
US 2010/0200145 A1     Aug. 12, 2010

(30) Foreign Application Priority Data

Mar. 2, 2009   (JP) ............................. P 2009-048650
Feb. 26, 2010  (JP) ............................. P2010-042129

(51) Int. Cl.
*A61F 13/15*     (2006.01)
*B32B 7/14*      (2006.01)

(52) U.S. Cl.
CPC ............. *A61F 13/15699* (2013.01); *B32B 7/14* (2013.01)
USPC ....................................................... 156/291

(58) Field of Classification Search
USPC ....................................................... 156/291
See application file for complete search history.

(56) References Cited

U.S. PATENT DOCUMENTS

| | | | |
|---|---|---|---|
| 5,389,168 A * | 2/1995 | Litchholt et al. | ................. 156/77 |
| 5,763,333 A | 6/1998 | Suzuki | |
| 6,972,011 B2 * | 12/2005 | Maeda et al. | ............ 604/385.01 |
| 7,037,301 B1 * | 5/2006 | Ohashi et al. | ............ 604/385.27 |
| 2008/0134487 A1 * | 6/2008 | Hartono | ......................... 29/428 |
| 2010/0212814 A1 | 8/2010 | Yamamoto | |

FOREIGN PATENT DOCUMENTS

| | | |
|---|---|---|
| CN | 1161195 A | 10/1997 |
| CN | 1160188 C | 8/2004 |
| EG | 2011091463 A | 9/2011 |
| EP | 1065047 A1 | 1/2001 |
| EP | 1410900 A1 | 4/2004 |
| JP | 3-195558 A | 8/1991 |
| JP | 6-21627 U | 3/1994 |
| JP | 6-104110 B2 | 12/1994 |
| JP | 10-80444 A | 3/1998 |
| JP | 2001-157691 A | 6/2001 |
| JP | 2001-157694 A | 6/2001 |
| JP | 200775277 A | 3/2007 |
| JP | 2008295641 A | 12/2008 |
| WO | 9104857 A1 | 4/1991 |

OTHER PUBLICATIONS

Official Action as issued on Feb. 28, 2013 in corresponding Chinese Patent Application No. 201080010122.9.
Colombian Official Action for counterpart application No. 11-126458 dated May 14, 2013.

(Continued)

*Primary Examiner* — Barbara J Musser
(74) *Attorney, Agent, or Firm* — Lowe Hauptman & Ham, LLP

(57) ABSTRACT

An adhesive is applied in such a curved trajectory that an angle formed by a tangent line and an axis falls within a range of ±90° in a plan view of a web obtained by the overlapping a first web and a second web. The tangent line is drawn at any point on the trajectory of the adhesive. The axis is orthogonal to a trailing side of a pressing region, in which the web is pressed by an upper roller, in a conveyance direction.

11 Claims, 6 Drawing Sheets

(56) References Cited

OTHER PUBLICATIONS

International Search Report and WO issued Jul. 20, 2010 in counterpart PCT Patent Application.
Office Action mailed Jul. 30, 2013 corresponds to Japanese patent application No. 2010-042129.
Office Action mailed Aug. 28, 2013 corresponds to Egyptian patent application No. 1466/2011.
Office Action mailed Sep. 26, 2013 corresponds to Chinese patent application No. 201080010122.9.
Extended European Search Report dated Dec. 4, 2013, corresponds to European patent application No. 10748876.9.

* cited by examiner

METHOD OF MANUFACTURING ABSORBENT ARTICLE

TECHNICAL FIELD

The present disclosure relates to a method of manufacturing an absorbent article formed of at least two continuous sheets laminated together.

BACKGROUND ART

An absorbent article, such as a pants-type disposable diaper, generally includes a front waistline region to be fitted to the front waistline of a wearer, a back waistline region to be fitted to the back waistline of the wearer, a crotch region to be fitted to the crotch of the wearer, and leg-surrounding regions (for example, leg holes) respectively at sides of the crotch region.

Such an absorbent article is formed mainly of: a liquid-permeable top sheet configured to come into contact with the skin of a wearer; a back sheet provided outside the top sheet; and an absorber provided between the top sheet and the back sheet and configured to absorb excretion of the wearer.

The top sheet, the back sheet, and the absorber are bonded together with adhesive. When an elastic member is disposed in the waistline regions or the leg-surrounding regions in order to enhance the fitness, the elastic member is also bonded by adhesive (refer to PTL 1).

PTL 1 describes a technique in which adhesive for bonding a top surface sheet, a bottom surface sheet, and an absorber is arranged in a spiral form continuous in a conveyance direction of a web during the manufacture.

According to the technique described in PTL 1, after adhesive is applied on side edge portions of a first web, an elastic member is disposed on the adhesive. Thereafter, a second web is overlaid onto the first web with the elastic member in between.

The inventors have discovered that, in the known technique, air may be trapped between any two of the first web, the adhesive, and the second web. In other words, an air pocket maybe formed. If the air permeability of the webs is high, the air in the air pocket is allowed to escape to the outside through the webs.

The inventors have discovered that if the air permeability of the webs is low, it is difficult for the air in the air pocket to escape to the outside of the webs.

Accordingly, when the webs are pressed by a roller in a subsequent step, the internal pressure of the air pocket increases. For this reason, it is conceivable that the risk of generation of creases in the webs and/or breakage of the webs is increased. It is desirable to avoid or to at least minimize such manufacturing defects that may lead to a decrease in the yield.

CITATION LIST

Patent Literature

PTL 1. Japanese Patent Application Publication No. 2001-157691 (p. 4, FIGS. 2 and 3)

SUMMARY

Therefore, the present invention has been made in consideration of the above problems. It is an object of the present invention to provide a method of manufacturing an absorbent article that is capable of preventing a decrease in the yield in manufacture when absorbent articles are manufactured by laminating webs each having a low air permeability.

A first aspect of the present invention is summarized as a method of manufacturing an absorbent article, said method comprising: applying adhesive on a first continuous web being continuously conveyed along a conveyance direction; overlaying a second web on the first continuous web; and pressing the first and the second webs against each other in at least a pressing region extending in a direction crossing the conveyance direction, in a plan view of the first continuous web and the second web, wherein the first continuous web and the second web comprises a liquid-impermeable sheet that is impermeable to liquid; and the adhesive is applied in such a curved trajectory that an angle formed between (i) a tangent line drawn at any point on the trajectory of the adhesive, and (ii) an axis orthogonal to a trailing side of the pressing region in the conveyance direction falls within a range of ±90° in the plan view.

According to the characteristics of the present invention, it is possible to provide a method of manufacturing an absorbent article that is capable of preventing a decrease in the yield in manufacture when absorbent articles are manufactured by laminating webs each having a low air permeability.

DETAILED DESCRIPTION

Hereinafter, a method of and an apparatus for manufacturing an absorbent article, according to one or more embodiments of the present invention, will be described with reference to the drawings.

Note that, in the following description of the drawings, same or similar reference signs denote same or similar elements and portions. In addition, it should be noted that the drawings are schematic and are not to scale unless otherwise specified. Therefore, specific dimensions and the like should be determined in consideration of the following description. Moreover, the drawings do not necessarily reflect the real-life dimensional relationships and ratios of components.

First, a structure of an absorbent article 1 according to one or more embodiments will be described with reference to FIG. 1 which is a partially cutaway perspective view showing the absorbent article 1. In the particularly illustrated embodiment, the absorbent article 1 is a pants-type disposal diaper for adults.

Figure 1:
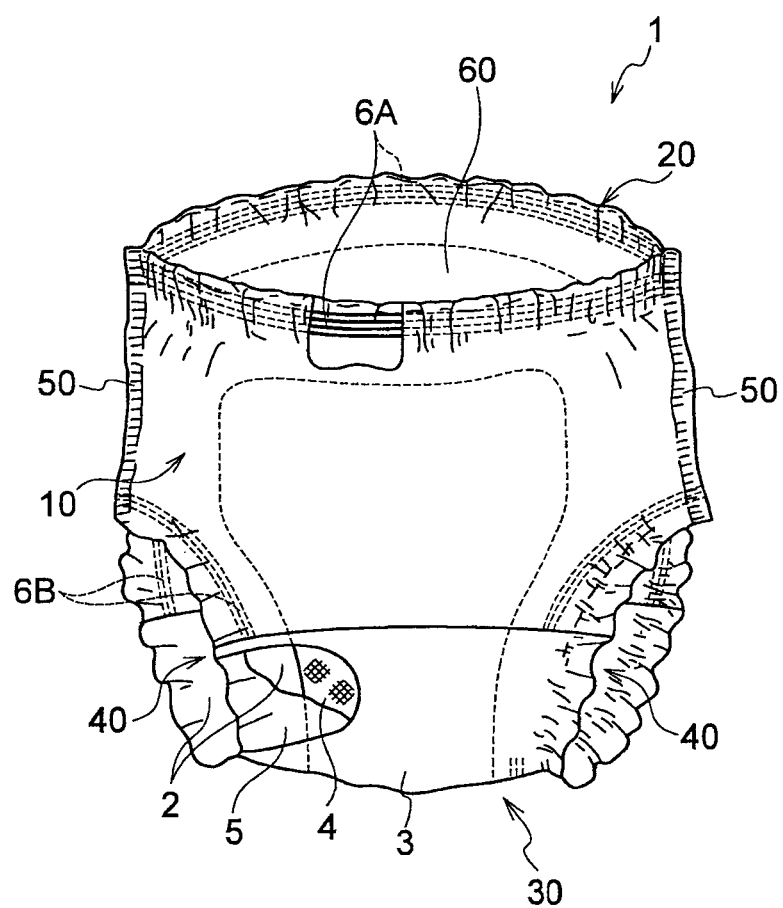
FIG. 1 is a partially cutaway, perspective view of an absorbent article according to one or more embodiments of the present invention.

As shown in FIG. 1, the absorbent article 1 is formed mainly of a top sheet 2, a back sheet 3, an absorber 4, and a waterproof sheet 5.

The top sheet 2 is configured to come into contact with a skin of a person wearing the absorbent article 1 (hereinafter, referred to as "wearer"). As the top sheet 2, a liquid-permeable sheet, such as a non-woven fabric or a perforated plastic film, is used.

The back sheet 3 is provided outside the top sheet 2, in other words, the back sheet is provided at the side farther from the wearer than top sheet 2. As the back sheet 3, a non-woven fabric or the like is used.

The absorber 4 is provided between the top sheet 2 and the back sheet 3, and is configured to absorb excretion of the wearer. As the absorber 4, a mixture of comminuted wood pulp and superabsorbent polymer particles, or the like, is used.

The waterproof sheet 5 is provided between the back sheet 3 and the absorber 4, and does not allow excretion of the wearer to permeate therethrough. The waterproof sheet 5 is a liquid-impermeable and moisture-permeable sheet that is impermeable to liquid but permeable to moisture.

The absorbent article 1 is provided with the top sheet 2, the absorber 4, the waterproof sheet 5 and the back sheet 3 in order, from the skin side of the wearer.

The absorbent article 1 as described above is formed by combining: a front waistline portion 10 to be fitted to the front waist of the wearer; a back waistline portion 20 to be fitted to the back waist of the wearer; and the crotch portion 30 to be fitted to the crotch of the wearer.

Note that, leg-surrounding openings 40 are formed respectively at sides of the crotch portion 30, and the legs of the wearer are to be inserted through the leg-surrounding openings 40.

The front waistline portion 10 and the back waistline portion 20 are united by joint portions 50, and thus form a waistline opening 60 to be fit around the body of the wearer.

A waist gather 6A made of rubber strands or the like having stretchability is provided in the peripheral edges of the front waistline portion 10 and the back waistline portion 20.

For example, the front waistline portion 10 and the back waistline portion 20 may be provided with the waist gather 6A to be thus stretchable in a cross direction crossing a front-to-back direction extending from the front waistline portion 10 to the back waistline portion 20, or may themselves be formed of sheets having stretchability to be thus stretchable in the cross direction.

The crotch portion 30 is provided between the front waistline portion 10 and the back waistline portion 20.

Leg gathers 6B each made of rubber strands or the like having stretchability are provided respectively at the sides of the crotch portion 30.

For example, the crotch portion 30 may be provided with the leg gathers 6B to be thus stretchable in the front-to-back direction of the absorbent article 1, or may itself be formed of a sheet having stretchability to be thus stretchable in the front-to-back direction of the absorbent article 1.

Next, a method of manufacturing the absorbent article 1 according to one or more embodiments will be described with reference to FIG. 2 which is an explanatory view for explaining a relevant part of the absorbent article manufacturing method.

Figure 2:
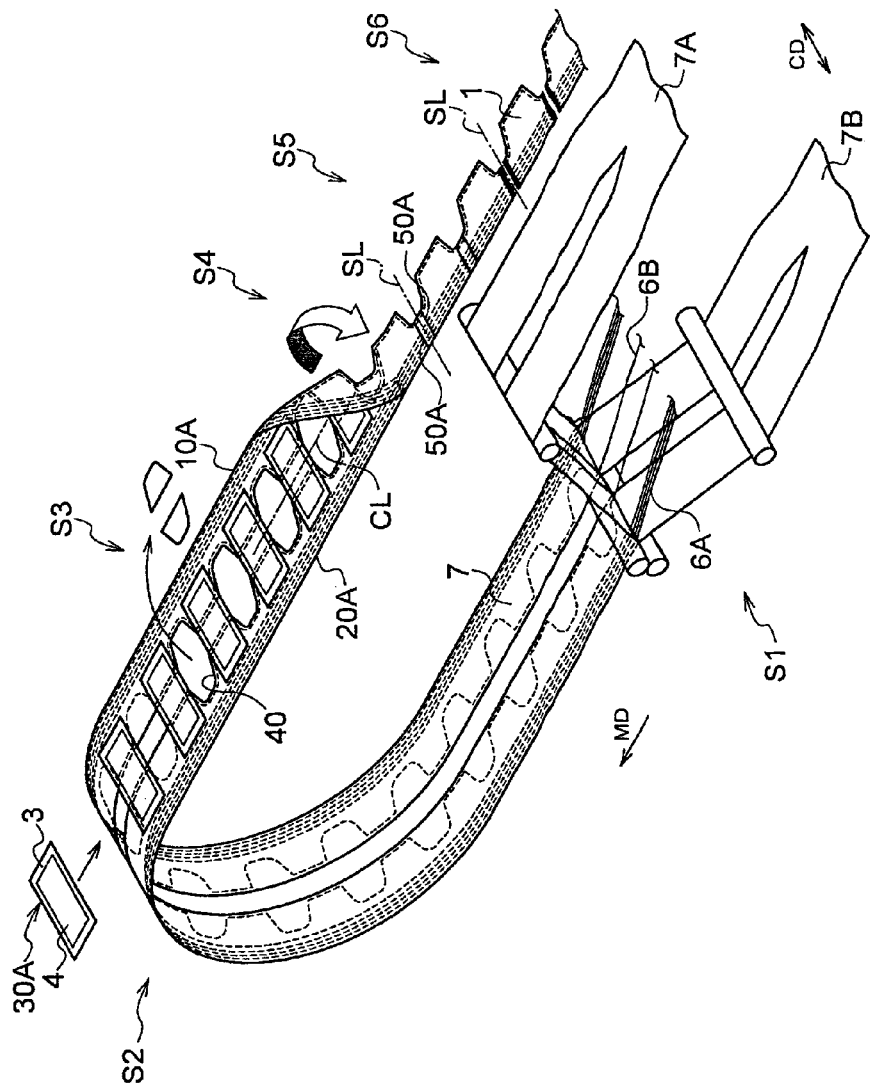
FIG. 2 is a diagram for explaining a method of manufacturing the absorbent article according to one or more embodiments.

As shown in FIG. 2, the method of manufacturing the absorbent article 1 includes at least a waistline forming step S1, an absorber transferring step S2, a leg-surrounding forming step S3, a folding step S4, a joining step S5, and a cutting step S6.

In the waistline forming step S1 a web 7 is formed by disposing gathers (the waist gather 6A and/or the leg gathers 6B) between a web 7A and a web 7B. The web 7 is to be processed into the front waistline portion 10 and the back waistline portion 20.

Note that, the web 7 (the webs 7A and 7B) being conveyed is stretchable in a cross direction CD (a width direction) orthogonal to a conveyance direction MD (Machine Direction) of the web 7.

In addition, the web 7 is asymmetrical with respect to a center line CL that bisects a width in the cross direction CD of the web 7 and extends in the conveyance direction MD of the web 7.

In the absorber transferring step S2, a crotch portion member 30A to be processed into the crotch portion 30 is transferred onto the web 7, specifically, between the front waistline portion 10 and the back waistline portion 20, after the waistline forming step S1. Note that, the crotch portion member 30A is formed of the back sheet 3 and the absorber 4.

In the leg-surrounding forming step S3, the leg-surrounding openings 40 (so-called leg holes) are formed by cutting the web 7 (the webs 7A and 7B) after the absorber transferring step S2.

Note that, the leg-surrounding openings 40 are not necessarily formed by cutting only the web 7 (the webs 7A and 7B), but may alternatively be formed by cutting the back sheet 3 forming the crotch portion member 30A together with the web 7A and the web 7B.

Here, the absorber transferring step S2 and the leg-surrounding forming step S3 may be performed in the reverse order.

In the folding step S4, the web 7 is folded in half along a folding line extending in the conveyance direction MD of the web 7, by bringing a side edge 10A of the front waistline portion 10 in the web 7 toward a side edge 20A of the back waistline portion 20 in the web 7, after the leg-surrounding forming step S3.

Note that, in the particularly illustrated embodiment, the folding line is the same as the center line CL. Moreover, the folding line does not necessarily coincide with the center line CL, and may be offset from the center line CL toward the side edge 10A or toward the side edge 20A.

In the joining step S5, the folded parts of the web 7 are joined at joint regions 50A to be processed into the joint portions 50 of the absorbent article 1 by an ultrasonic treatment or a heat treatment, after the folding step S4.

Note that the joint regions 50A respectively indicate regions at both sides of an imaginary line SL in the conveyance direction MD. The imaginary line SL indicates a cutting line extending in the width direction CD.

In the cutting step S6, the web 7 in which the joint regions 50A have been joined is cut along the imaginary line SL after the joining step S5. As a result, the absorbent article 1 is manufactured.

In the waistline forming step S1, the web 7A and the web 7B are overlaid one upon another, sandwiching the waist gathers 6A and/or the leg gathers 6B therebetween. Then, the web 7A and the web 7B are joined to each other with adhesive or the like.

In addition, in the absorber transferring step S2, the crotch portion member 30A transferred onto the web 7 (the web formed of the overlaid webs 7B and 7A) having the leg-surrounding openings 40 formed therein is joined to the web 7 with adhesive or the like.

Herein below, a description will be given of an apparatus for use in any step in which webs are joined to each other or a web and a member (a sheet or a gather) are joined to each other, such as the waistline forming step S1 and the absorber transferring step S2.

Figure 3:
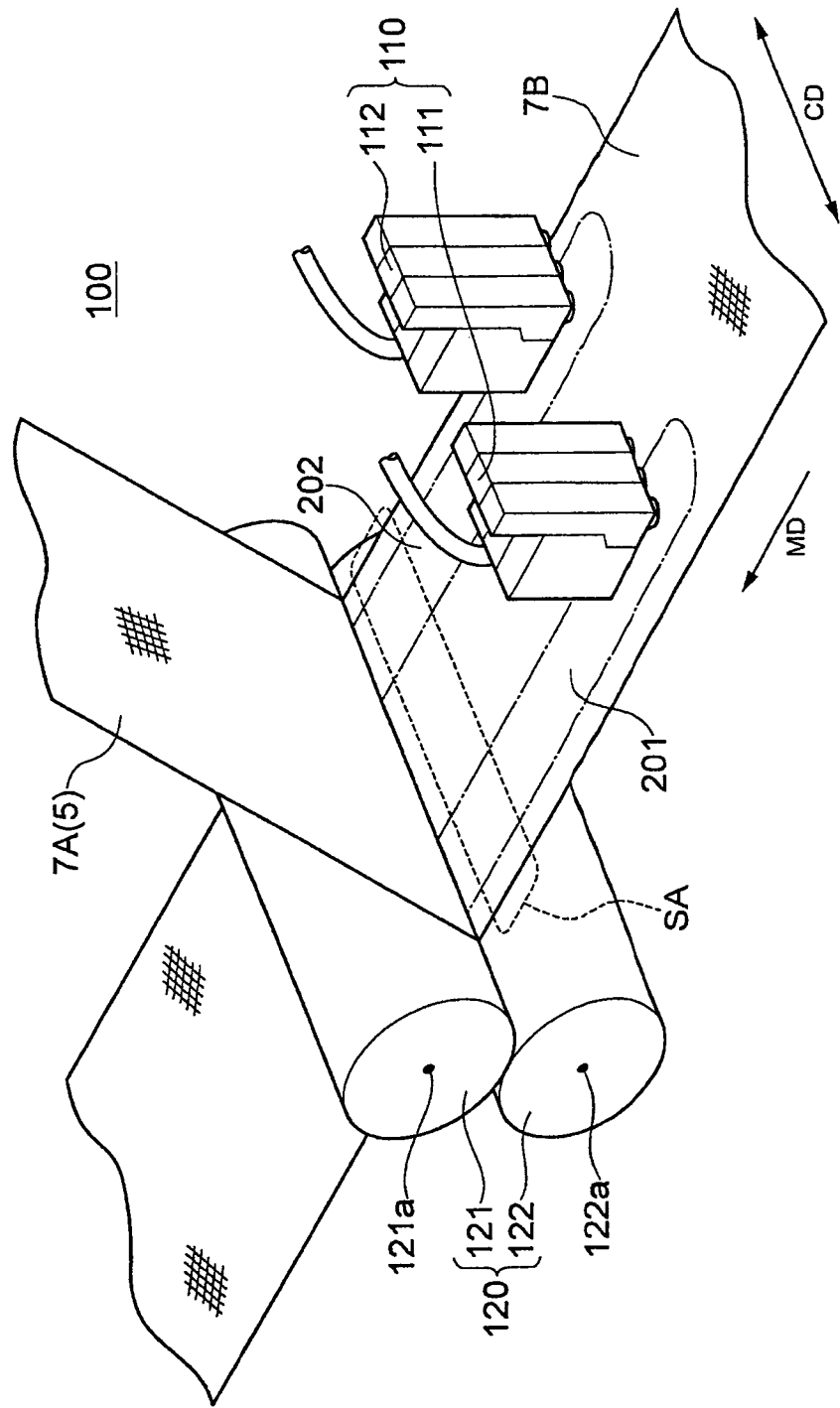
FIG. 3 is a perspective view of a relevant part of an apparatus for manufacturing the absorbent article according to one or more embodiments.

FIG. 3 is a perspective view of a relevant part of an apparatus for manufacturing the absorbent article 1 according to one or more embodiments.

The manufacturing apparatus 100 includes: an application mechanism 110 configured to apply a flowable adhesive onto the web 7B (first continuous web); and a press mechanism 120 configured to place the web 7A (second continuous web) or the absorber 4 onto the web 7B having the adhesive applied thereon, and to then press the webs 7A and 7B (or the web 7B and absorber 4) against each other.

The application mechanism 110 includes an ejecting unit 111 and an ejecting unit 112 each configured to eject adhesive onto the web 7B.

Each of the ejecting unit 111 and the ejecting unit 112 is configured to eject the flowable adhesive onto the web 7B. In other words, each of the ejecting unit 111 and the ejecting unit 112 is capable of placing the adhesive on the web 7B without coming into contact with the web 7B.

The adhesive ejected from the ejecting unit 111 forms an adhesion region 201 on the web 7B. The adhesive ejected from the ejecting unit 112 forms an adhesion region 202 on the web 7B.

In other words, the application mechanism 110 is configured to perform an application step in the conveyance direction MD of the web 7B, in which the adhesive is applied onto the web 7B continuously in the conveyance direction MD.

Each of the ejecting mechanism 111 and the ejecting mechanism 112 includes adhesive nozzles (not shown).

In addition, each of the ejecting mechanism 111 and the ejecting mechanism 112 includes air nozzles (not shown) configured to blow air in a plurality of directions to the adhesive ejected from the adhesive nozzles.

Each of the ejecting mechanism 111 and the ejecting mechanism 112 is configured to change the trajectory of the adhesive in the air, by blowing air as appropriate in a plurality of directions to the adhesive ejected from the adhesive nozzles.

This configuration enables each of the ejecting mechanism 111 and the ejecting mechanism 112 to change the shape of the adhesive placed on the web 7B. The shape of the adhesive placed on the web 7B will be described later.

The press mechanism 120 includes an upper roller 121 and a lower roller 122.

The upper roller 121 and the lower roller 122 are configured to hold the web 7B and the web 7A (for example, the waterproof sheet 5) which is overlaid with the web 7B from above and/or below.

The upper roller 121 and the lower roller 122 are configured to press the web 7A and the web 7B against each other, by holding the web 7A and the web 7B in a direction crossing the plane of the webs 7A and 7B.

The upper roller 121 and the lower roller 122 form a pressing region extending in a direction crossing the conveyance direction MD on the webs 7A and 7B.

In the embodiment, a rotational axis 121a of the upper roller 121 and a rotational axis 122a of the lower roller 122 are parallel to the cross direction CD orthogonal to the conveyance direction MD.

In other words, the press mechanism 120 is configured to perform a pressing step in which the overlaid webs 7A and 7B are pressed against each other in the pressing region extending in the cross direction CD.

FIG. 3 shows a case where the webs 7B and 7A are laminated. An example of the web 7B is the back sheet 3, and an example of the web 7A is the waterproof sheet 5. A step of placing one or more elastic members (e.g., a gather 6) on the adhesion region 201 and/or the adhesion region 202 formed on the back sheet 3 may be subsequently executed.

The waterproof sheet 5 is a liquid-impermeable and moisture-permeable sheet that is impermeable to liquid but permeable to moisture.

The air permeability of the waterproof sheet 5 is, in some embodiments, not more than 950 cc/cm$^2$·sec, and, in further embodiments, may be between 300 cc/cm$^2$·sec and 800 cc/cm$^2$·sec, and may be between 400 cc/cm$^2$·sec and 700 cc/cm$^2$·sec when measured by the Gurley test.

Next, the shape of the adhesive placed in the adhesion region 201 and the adhesion region 202 will be described.

Figure 4:
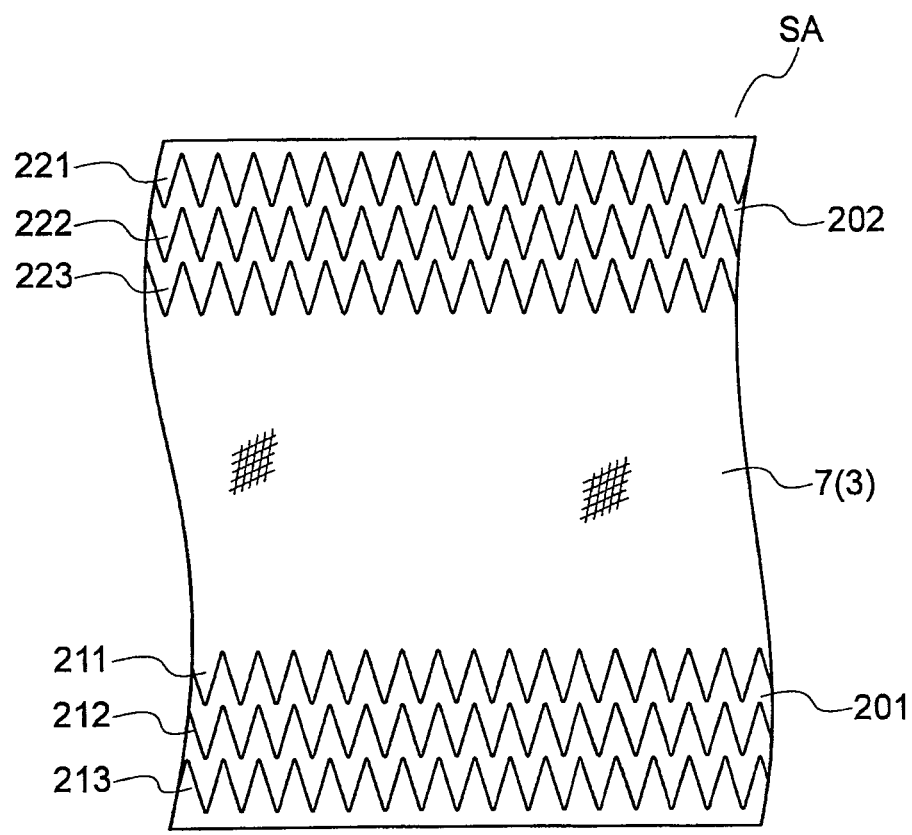
FIG. 4 is an enlarged view of a region SA shown in FIG. 3.

FIG. 4 is an enlarged view of a region SA shown in FIG. 3. FIG. 4 shows the shape of the adhesive placed in the adhesion region 201 and the adhesion region 202.

In one or more embodiments, a plurality of lines of adhesive each having a waveform continuing in the conveyance direction MD are placed in each of the adhesion region 201 and the adhesion region 202.

Specifically, in the particularly illustrated embodiment, three lines of adhesive 211, 212, and 213 are placed in the adhesion region 201. On the other hand, three lines of adhesive 221, 222, and 223 are placed in the adhesion region 202.

Note that the number of lines of adhesive may be changed as appropriate by changing the number of adhesive nozzles included in each of the ejecting portion 111 and the ejecting portion 112.

In one or more embodiments, the shapes of the lines of adhesive placed on the adhesion region 201 or the adhesion region 202 are identical.

Accordingly, the shape of the lines of adhesive placed in each of the adhesion regions 201 and 202 will be described herein below by using, as an example, the line of adhesive 211 among the three lines of adhesive 211, 212, and 213 placed in the adhesion region 201.

Figure 5:
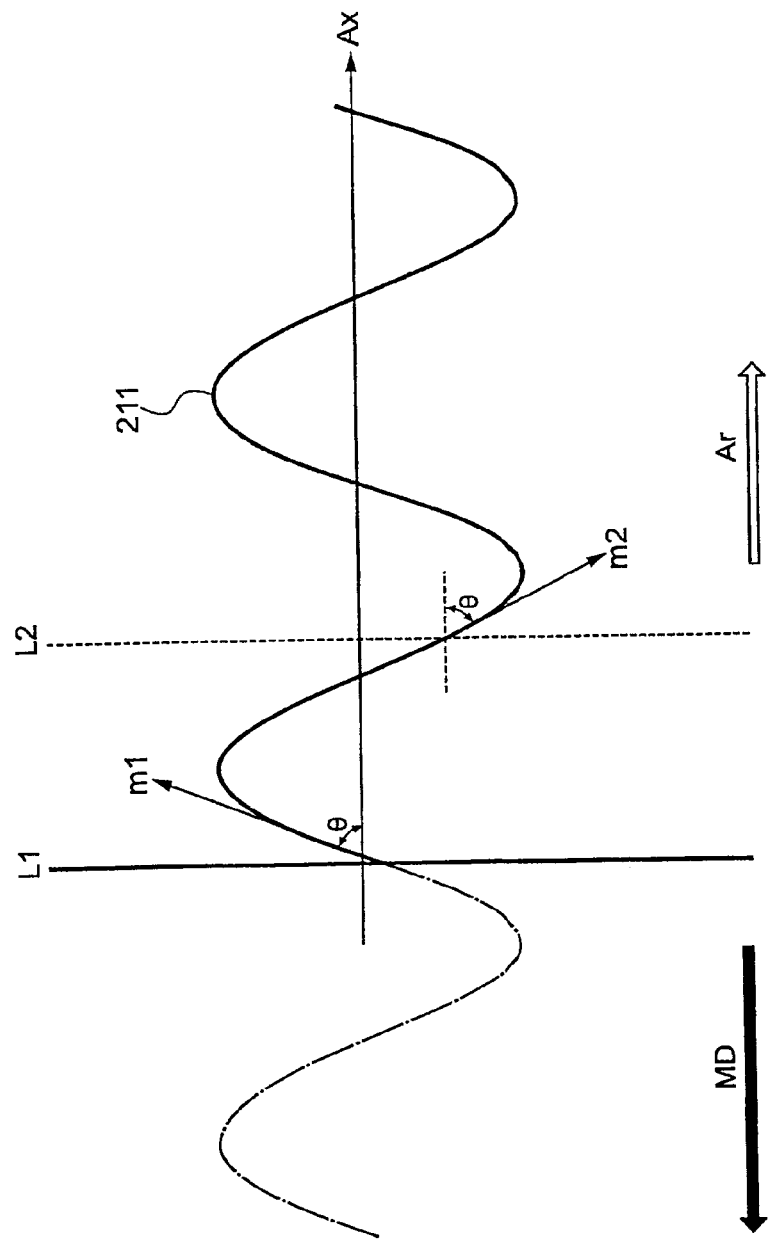
FIG. 5 is a diagram for explaining a shape of adhesive placed in an adhesion region in accordance with one or more embodiments.

FIG. 5 is a diagram for explaining the shape of the line of adhesive placed in each of the adhesion regions 201 and 202.

A line L1 represented by a solid line in FIG. 5 indicates a trailing side of the pressing region in the conveyance direction MD at a time point t1, the pressing region being formed in the webs 7A and 7B by the upper roller 121 and the lower roller 122. In other words, the line L1 indicates a position at which the upper roller 121 presses the web 7A at the time point t1.

A line L2 represented by a broken line in FIG. 5 indicates a position at which the upper roller 121 presses the web 7A at a time point t2 after the time point t1. The time period between t1 and t2 is Δt.

FIG. 5 shows that the position at which the upper roller 121 presses the web 7A moves along an axis Ax extending in the opposite direction to the conveyance direction MD as the webs 7A and 7B move in the conveyance direction MD.

In one or more embodiments, the line of adhesive 211 is applied onto the web 7B in such a curved shape that the angle θ formed by each of tangent lines m1 and m2 with the axis orthogonal to the line L1 or the line L2 at the positions where the upper roller 121 presses the web 7A falls within the range of ±90° in the plan view of the overlaid webs 7A and 7B.

Here, the tangent lines m1 and m2 are those drawn at any points on the line of adhesive 211 in the plan view.

FIG. 5 shows a case where the rotational axis 121a of the upper roller 121 is parallel to the cross direction CD, which is orthogonal to the conveyance direction MD.

In other words, the position (the line L1 or the line L2) at which the upper roller 121 presses the web 7A is parallel to the width direction of the webs 7A and 7B conveyed.

However, the rotational axis 121a of the upper roller 121 and the rotational axis 122a of the lower roller 122 shown in FIG. 5 do not have to be parallel to the cross direction CD.

Figure 6:
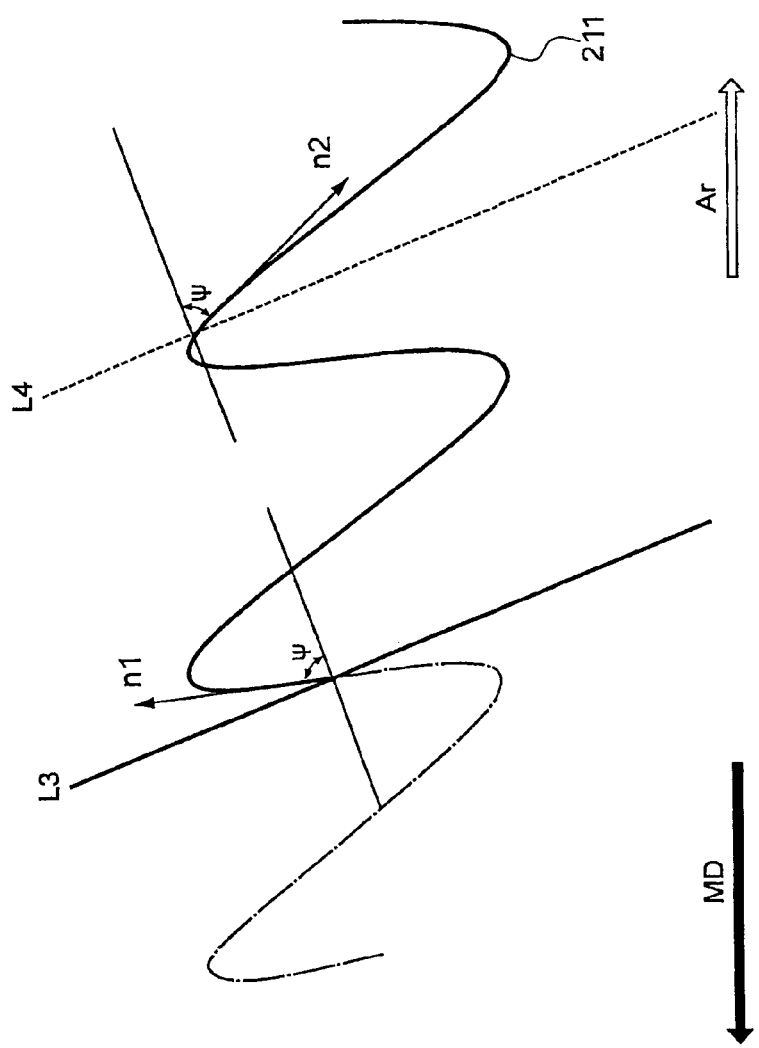
FIG. 6 is a diagram for explaining another shape of adhesive placed in the adhesion region.

FIG. 6 is a diagram for explaining another shape of the line of adhesive placed in each of the adhesion regions 201 and 202. FIG. 6 shows a case where the rotational axis 121a of the upper roller 121 is arranged in a direction crossing but oblique to the conveyance direction MD.

In other words, the position (the line L1 or the line L2 in FIG. 5) at which the upper roller 121 presses the web 7A is at a predetermined angle to the width direction (cross direction CD) of the webs 7A and 7B conveyed in FIG. 6.

A line L3 represented by a solid line in FIG. 6 indicates a trailing side of a pressing region in the conveyance direction MD at a time point t1, the pressing region being formed in the webs 7A and 7B by the upper roller 121 and the lower roller 122. In other words, the line L3 indicates a position at which the upper roller 121 presses the web 7A at the time point t1.

A line L4 represented by a broken line in FIG. 6 indicates a position at which the upper roller 121 presses the web 7A at a time point t2 after the time point t1. The time period between t1 and t2 is Δt.

In the example shown in FIG. 6, the upper roller 121 is arranged at the predetermined angle to the conveyance direction MD, and the line of adhesive 211 is applied onto the web 7B in such a curved shape that the angle Ψ formed by each of tangent lines n1 and n2 with the axis orthogonal to the line L3 or the line L4 at the positions where the upper roller 121 presses the web 7A falls within the range of ±90° in the plan view of the overlaid webs 7A and 7B.

Here, the tangent lines n1 and n2 are those drawn at any points on the line of adhesive 211 in the plan view.

As described above, with the manufacturing apparatus 100, the line of adhesive 211 is applied onto the web 7B in such a curved shape that the angle formed by each of the tangent lines m1 and m2 at any points on the line of the adhesive 211 with the axis orthogonal to the position (the line L1 or the line L2) at which the upper roller 121 presses the web 7A falls within the range of ±90° in the plan view of the overlaid webs 7A and 7B.

In other words, the line of adhesive 211 does not cross itself. In addition, the position (the line L1 or L2) at which the upper roller 121 presses the web 7A and the line of adhesive 211 do not form any closed region.

That is, all the regions defined by the position (the line L1 or L2) at which the upper roller 121 presses the web 7A and the line of adhesive 211 are open in the direction of the axis Ax.

A low air permeability means that a material of the sheet has a large mass per unit area and a small porosity. That is, air is unlikely to penetrate through the sheet.

In general, the back sheet 3 of a sheet having an air permeability of not more than 950 cc/cm²·sec allows a small amount of air to penetrate through the back sheet 3 and escape to the outside.

For this reason, if any closed space is formed by the adhesive, the amount of air that is allowed to penetrate through the back sheet 3 and escape to the outside is significantly decreased. As a result, the pressing with a roller increases the internal pressure of any trapped air pocket.

By employing the line of adhesive 211 applied by the manufacturing apparatus 100 in accordance with the disclosed embodiments, when the webs 7A and 7B are held by the upper roller 121 and the lower roller 122, air existing between the web 7A and the web 7B can escape to the outside in a direction Ar as shown in FIG. 5 and FIG. 6.

Accordingly, air is not trapped among the web 7A, the adhesive 211, and the web 7B. In other words, no air pocket is formed.

For this reason, when an absorbent article is manufactured by laminating webs each having a small air permeability, it is possible to prevent generation of crease in the web, breakage of the web, and the like due to formation of an air pocket. Furthermore, it is possible to prevent a decrease in the yield in manufacture.

As described above, the details of several embodiments have been exemplarily disclosed. However, it should not be understood that the description and drawings which constitute part of this disclosure limit the present invention. From this disclosure, various alternative embodiments, examples, and operation techniques will be easily found by those skilled in the art.

For example, the following additional embodiments can be envisaged. Specifically, the absorbent article manufactured in accordance with the present invention is not limited to a disposable diaper, but may be an absorbent article such as a sanitary napkin or a panty liner, for example, and also may be any product other than the absorbent articles.

In the above disclosed embodiments, both of the waterproof sheet 5 and the back sheet 3 are described to be moisture-permeable sheets.

Alternatively, a single sheet that is impermeable to liquid but permeable to moisture may be used in place of the waterproof sheet 5 and the back sheet 3. Moreover, either one of the waterproof sheet 5 and the back sheet 3 may be a liquid-impermeable sheet.

Furthermore, the manufacturing apparatus 100 according to the above disclosed embodiments may be used for a step of bonding a liquid-impermeable and moisture-permeable sheet and an absorber together.

The manufacturing apparatus 100 according to the above disclosed embodiments is not limited for use in the joining of webs and the joining of a web and a member in the waistline forming step S1 and the absorber transferring step S2.

For example, the manufacturing apparatus 100 may be used in a step of bonding an elastic member provided in the waistline region or the leg-surrounding openings in order to improve the fitness of the absorbent article onto the wearer.

In the above disclosed embodiments, the lines of adhesive placed in any of the adhesion region 201 and the adhesion region 202 have been described to have the same shape, but may have shapes different from each other.

In this case, the shapes of the lines of adhesive are determined in such a manner that no occluded region is formed by adjacent lines of adhesive interfering with each other on the web 7B.

As described above, the present invention naturally includes various embodiments which are not described herein. Accordingly, the technical scope of the present invention should be determined only by the matters to define the invention in the scope of claims regarded as appropriate based on the description.

The entire content of Japanese Patent Applications 2009-048650 (filed on Mar. 2, 2009) and 2010-042129 (filed on Feb. 26, 2010) incorporated herein by reference.

INDUSTRIAL APPLICABILITY

Therefore, since the method of manufacturing absorbent article of the present invention is capable of manufacturing an absorbent articles that is capable of preventing a decrease in the yield in manufacture when absorbent articles are manufactured by laminating webs each having a low air permeability, it is useful in manufacturing technology for absorbent articles.

REFERENCE SIGNS LIST 1 absorbent article
2 top surface sheet
3 bottom surface sheet
4 absorber
5 waterproof sheet
6 gather
6A waist gather
6B leg gather
7A, 7B web
10 front waistline portion
20 back waistline portion
30 crotch portion
40 leg-surrounding openings
50 joint portion
60 waistline openings
100 manufacturing apparatus
110 application mechanism
111 ejecting portion
112 ejecting portion
120 press mechanism
121 upper roller
121a rotational axis
122 lower roller
122a rotational axis
201, 202 adhesion region
211, 212, 213 line of adhesive
221, 222, 223 line of adhesive

The invention claimed is:

1. In a process of manufacturing an absorbent article, a method of laminating first and second webs comprising, while conveying the webs along a conveyance direction:
　applying adhesive between the webs; and
　pressing the webs against each other in at least a pressing region extending in a direction crossing the conveyance direction,
　wherein
　　the adhesive is applied in such a curved trajectory that the trajectory and a trailing side of the pressing region in the conveyance direction form no closed region, thereby permitting any air strapped between the webs to escape, and
　　the trailing side of the pressing region in the conveyance direction is oblique to the conveyance direction.

2. The method according to claim 1, wherein all the regions defined by the trailing side of the pressing region and the trajectory are open in a direction opposite to the conveyance direction, thereby permitting any air strapped between the webs to escape in said opposite direction.

3. The method according to claim 1, wherein both of the first and second webs are liquid-impermeable.

4. The method according to claim 1, wherein said pressing the webs against each other defines a laminated sheet which is liquid-impermeable to liquid but permeable to vapor.

5. A method of manufacturing an absorbent article, said method comprising:
　applying adhesive on a first continuous web being continuously conveyed along a conveyance direction;
　overlaying a second web on the first continuous web; and
　pressing the first and the second webs against each other to define a laminated sheet in at least a pressing region extending in a direction crossing the conveyance direction, in a plan view of the first continuous web and the second web,
　wherein
　　the laminated sheet is liquid-impermeable to liquid but permeable to vapor,
　　the adhesive is applied in such a curved trajectory that an angle formed between (i) a tangent line drawn at any point on the trajectory of the adhesive, and (ii) an axis orthogonal to a trailing side of the pressing region in the conveyance direction falls within a range of ±90° in the plan view, and
　　the trailing side of the pressing region in the conveyance direction is arranged in a direction crossing but oblique to the conveyance direction.

6. The method according to claim 5, wherein at least one of the first and second webs is liquid-impermeable.

7. The method according to claim 5, wherein the adhesive is applied onto the first continuous web and contacts with the second web when the first and the second webs are pressed against each other.

8. The method according to claim 5, wherein both of the first web and the second web are liquid-impermeable.

9. The method according to claim 5, wherein the adhesive is flowable.

10. The method according to claim 9, wherein the applying adhesive comprises blowing air in a plurality of directions at the applied adhesive to define the curved trajectory of the adhesive.

11. The method according to claim 5, wherein, in said applying adhesive on the first continuous web, the adhesive does not cross itself.

\* \* \* \* \*